US006361816B1

(12) United States Patent
Amari

(10) Patent No.: US 6,361,816 B1
(45) Date of Patent: Mar. 26, 2002

(54) USE OF AN EXTRACT FROM THE LEAVES OF OLEA EUROPEA AS AN ANTIRADICAL

(75) Inventor: Giorgio Amari, Milan (IT)

(73) Assignee: B & T S.R.L., Milan (IT)

(*) Notice: Subject to any disclaimer, the term of this patent is extended or adjusted under 35 U.S.C. 154(b) by 0 days.

(21) Appl. No.: 09/661,302

(22) Filed: Sep. 13, 2000

Related U.S. Application Data

(62) Division of application No. 09/250,163, filed on Feb. 16, 1999, now Pat. No. 6,147,637.

(30) Foreign Application Priority Data

Feb. 19, 1998 (IT) .......................................... MI98A0317

(51) Int. Cl.⁷ .......................... A01N 65/00; A23L 1/06; A23L 1/30; A23L 3/3472
(52) U.S. Cl. ........................ 426/542; 424/769; 424/744
(58) Field of Search ................................ 424/769, 774; 426/542, 321

(56) References Cited

U.S. PATENT DOCUMENTS 5,714,150 A   2/1998  Nachman 6,146,637 A  * 11/2000  Amari ........................ 424/769

FOREIGN PATENT DOCUMENTS

| FR | 2588159 | 4/1987 |
| WO | WO 9623484 | 8/1996 |
| WO | WO 9732947 | 9/1997 |

OTHER PUBLICATIONS

B. LeTutour et al., "Antioxidative Activities of Olea Europaea Leaves and Related Phenolic Compounds," Phytochemistry, vol. 31, No. 4, 1992, pp. 1173–1178.
J. Giese, "Antioxidants: Tools for Preventing Lipid Oxidation," Food Technology, Nov. 1996, pp. 73, 74, 76, 78, 80.
F. Visioli et al., "Oleuropein Protects Low Density Lipoprotein from Oxidation," Life Sciences, vol. 55, No. 24, 1994, pp. 1965–1971.

* cited by examiner

Primary Examiner—Herbert J. Lilling
(74) Attorney, Agent, or Firm—Young & Thompson

(57) ABSTRACT

The use of an extract from the leaves of *Olea Europea* as an antiradical. Preferably, the extract is added to a preparation wherein the concentration of the extract does not exceed 0.5% by weight. The extract can be used both for preparing cosmetic products, such as cosmetic creams—particularly sun protection creams—and for preparing alimentary products—particularly dietetic products.

9 Claims, No Drawings

USE OF AN EXTRACT FROM THE LEAVES OF OLEA EUROPEA AS AN ANTIRADICAL

This application is a divisional of application Ser. No. 09/250,163, filed on Feb. 16, 1999 now U.S. Pat. No. 6,147,637, the entire contents of which are hereby incorporated by reference.

BACKGROUND OF THE INVENTION

1. Field of the Invention

The present invention concerns the use of an extract from the leaves of *Olea Europea* (commonly called olive tree), as an antiradical, particularly in the cosmetic and alimentary fields.

2. Prior Art

The use of antioxidant substances, apt to prevent the forming of free radicals, is rather widespread both in the alimentary and in the cosmetic fields.

In the alimentary field, the oxidizing action is what causes the food to deteriorate. It is hence frequent to add into foods antiradicals for alimentary use, such as acetylsalicylic acid and its esters, or 1-ascorbic acid, which develop an antioxidant action.

In the cosmetic field, the antiradicalic substances are above all used for sun protection creams. In fact, the ultraviolet irradiation causes the forming of free radicals which determine a sort of skin ageing and, after a prolonged exposure, may even lead to damages of neoplastic nature.

The extract from the leaves of *Olea Europea*, already known since quite a long time, consists of an extremely complex mixture of orcanic components: most of them have not yet been identified. Among the components which have been identified, the main ones are oleoeuropeine and verbacoside. These two bitter glucosides are cited in literature and, precisely, in the "Gazzetta Chimica Italiana" (1960—Vol. 90, page 1449) by L. Panizzi, M. L. Scarpati and E. G. Oriente, and in the "Journal of Food Science" (1993—Vol. 58, page 347) by M. Brenes, M. C. Duran and A. Garrido. Particularly oleoeuropeine is known as an antimicrobic substance, as resulting from the "Journal of Applied Bacteriology" (1970—Vol. 33, page 72 and 1972—Vol. 35, page 559) by B. Juven and Y. Hems.

It has now been found that the extract from the leaves of *Olea Europea*, which contains more than 7% of oleoeuropeine, has considerable preserving properties. Such properties derive, not only from the known antimicrobic action cited heretofore, but also from a considerable antiradicalic action—never evidenced up-to-date and, as a matter of fact, even unexpected—which said extract has been found to develop.

SUMMARY OF THE INVENTION

The present invention has been conceived on the basis of said principle and actually concerns the use of an extract from the leaves of *Olea Europea* as an antiradical.

Said antiradicalic action provides great advantages in the preparing of cosmetics or foods.

In the cosmetic field, said extract finds its ideal use especially in sun protection creams.

In the alimentary field, said extract is mainly used for preparing dietetic products.

Preferably, said extract is added to the cosmetic or alimentary preparation in a concentration not exceeding 0.5% by weight.

The extract is prepared by dipping the leaves into water, and subjecting the infusion to ultrasounds, so as to accelerate the extraction. This allows to obtain an extract containing at least 7% by weight of oleoeuropeine. It is deemed that the antiradicalic action is partly produced by oleoeuropeine and partly by other substances synergistically acting therewith.

The extract thus obtained is added to the cosmetic or alimentary preparation in a concentration not exceeding 0.5% by weight, and then mixed therewith in any known manner.

DESCRIPTION OF THE PREFERRED EMBODIMENT

In the cosmetic field, the action of the extract according to the present invention develops in the cosmetic product to which it is added as well as on the tissues on which said product is applied. It is particularly helpful in various types of cosmetic creams, and even more helpful in the case of sun protection creams. Such products bring the extract in contact with the skin and, in the case of certain preparations, they cause it to penetrate into the inner skin layers. In all such cases, the active substances contained in the extract from the leaves of *Olea Europea* stop the forming, in the tissues, of the free radicals determined by the action of ultraviolet irradiation—whether it be of natural origin, or artificially produced—so as to protect the skin from a premature ageing and from any possible phenomena of the neoplastic type. Moreover, as mentioned above, said extract also acts onto the components of the cosmetic preparation, preserving it from decay due to radicalic oxidation and considerably lengthening its life. As can be easily understood, this type of action is particularly appreciated and effective in the case of sun protection creams, which are used in conditions of highly strong UV rays, whereby the forming of free radicals is very likely to occur.

In the alimentary field, the extract is used—according to the invention—to delay the deterioration of the most perishable foodstuffs, for example long-life fruit juices or other soft drinks, jams and tinned fruits and vegetables, sacked meats and sausages, and particularly for the preparing of dietetic products.

According to the present invention, the use in the alimentary field is possible in that the extract contains sugars and agliconic derivatives, all of which are edible. Also in this case it, is not necessary to exceed a concentration of 0.5% by weight, seen that the extract develops a synergistic action with the antiradicalic substances usually soluble in the lipids, such as tocopherols. It is however advisable to proportion each time the concentration according to the particular food being preserved. The antiradicalic action develops both directly and indirectly, through a protective action on the tocopherols.

Since the antiradicalic action is mostly developed by the agliconic components, it is totally independent from the presence of enzymes. It may, on the contrary, develop both on the hydrosoluble and on the liposoluble substances, seen that aglicone is liposoluble: this allows to use the extract according to the present invention also in the hot-prepared alimentary products. The water-solubility of the extract of *Olea Europea* is remarkably higher than the effective dose; though being very low in the lipids, the solubility is however already sufficient to give an adequate protection to the alimentary substances also in the lipidic phase.

The present invention will now be described in further detail, with reference to an experimental test thereof, reported by mere way of non-limiting example.

EXPERIMENTAL TEST

The antiradicalic properties of the extract from the leaves of *Olea Europea* have been verified through the test proposed by Chaboun et al., in BBA (1990—Vol. 1042, page 324).

Said test is based on the fact that copper is a reactive radical which produces peroxidation. If lipoproteins are treated with copper, the polyunsaturated fatty acids contained therein are considerably removed.

Two plasma samples were incubated, respectively containing 3 and 0.3 mg/l of extract from the leaves of *Olea Europea*, and copper sulphate was added thereto in order to produce their peroxidation. The treatment with copper sulphate was also carried out on a plasma sample containing no such extract: 80% of the eicosapentanoic acid, 80% of the docosaesanoic acid, 80% of the linolenic acid and 50% of the arachidonic acid, disappeared from this last sample. Whereas, in the two plasma samples treated with the extract according to the invention, the concentration of said fatty acids remained unvaried: this proves that the antiradicalic action of the extract from the leaves of *Olea Europea* is very strong already at low concentrations.

What is claimed is:

1. A method of preventing the formation of free radicals in an alimentary product, which comprises adding to the alimentary product an antiradical effective amount of an aqueous extract from the leaves of *Olea Europea*, said extract containing at least 7% by weight of oleoeuropeine, and the concentration of said extract not exceeding 0.5% by weight.

2. The method according to claim 1, wherein the alimentary product is a dietetic product.

3. The method according to claim 1, wherein the alimentary product is a preserved food.

4. The method according to claim 3, wherein the preserved food is jam.

5. The method according to claim 3, wherein the preserved product is canned fruits or canned vegetables.

6. The method according to claim 1, wherein the alimentary product is meat.

7. The method according to claim 1, wherein the alimentary product is a beverage.

8. The method according to claim 7, wherein the beverage is a soft drink.

9. The method according to claim 7, wherein the beverage is a fruit juice.

\* \* \* \* \*